US009675821B2

(12) United States Patent
Ostrovsky et al.

(10) Patent No.: US 9,675,821 B2
(45) Date of Patent: Jun. 13, 2017

(54) DEVICE FOR THERMAL TREATMENT OF TISSUE AND FOR TEMPERATURE MEASUREMENT OF TISSUE PROVIDING FEEDBACK

(75) Inventors: Isaac Ostrovsky, Wellesley, MA (US);
Victor Shukhat, Canton, MA (US);
Alfred P. Intoccia, Nashua, NH (US);
Jon T. McIntyre, Newton, MA (US);
Ty Fairneny, Marlborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2102 days.

(21) Appl. No.: 11/374,811

(22) Filed: Mar. 14, 2006

(65) Prior Publication Data
US 2007/0219602 A1    Sep. 20, 2007

(51) Int. Cl.
*A61N 7/02* (2006.01)
*A61B 17/00* (2006.01)
*A61N 7/00* (2006.01)
*A61B 90/00* (2016.01)

(52) U.S. Cl.
CPC .... *A61N 7/022* (2013.01); *A61B 2017/00084* (2013.01); *A61B 2090/378* (2016.02); *A61N 2007/0078* (2013.01)

(58) Field of Classification Search
CPC .... A61B 2017/00084; A61B 2090/378; A61N 2007/0078; A61N 7/022
USPC ............... 600/438, 459, 462, 466, 437, 442; 601/1–3
See application file for complete search history.

(56) References Cited

U.S. PATENT DOCUMENTS

| 4,757,821 | A | * | 7/1988 | Snyder | 600/453 |
|---|---|---|---|---|---|
| 4,821,838 | A | * | 4/1989 | Chen | 181/175 |
| 4,938,217 | A | * | 7/1990 | Lele | 601/3 |
| 4,960,109 | A | * | 10/1990 | Lele | 600/549 |
| 5,190,517 | A | * | 3/1993 | Zieve et al. | 604/22 |
| 5,735,280 | A | * | 4/1998 | Sherman et al. | 600/1 |
| 5,873,845 | A | * | 2/1999 | Cline et al. | 601/3 |
| 6,083,232 | A | * | 7/2000 | Cox | 606/128 |
| 6,235,024 | B1 | * | 5/2001 | Tu | 606/41 |
| 6,364,531 | B1 | | 4/2002 | Lamle | |
| 6,506,171 | B1 | * | 1/2003 | Vitek et al. | 601/2 |
| 7,247,155 | B2 | * | 7/2007 | Hoey et al. | 606/34 |
| 7,291,110 | B2 | * | 11/2007 | Sahatjian | 600/439 |

(Continued)

FOREIGN PATENT DOCUMENTS

| EP | 0 643 982 | 3/1995 |
|---|---|---|
| WO | 2005/072391 | 8/2005 |

*Primary Examiner* — Tse Chen
*Assistant Examiner* — Vani Gupta
(74) *Attorney, Agent, or Firm* — Brake Hughes Bellermann LLP

(57) ABSTRACT

A device for heating tissue, comprises a housing sized for insertion through a naturally occurring body orifice to a target location within a lumen and a heat generating element within the housing focusing thermal energy on a target area separated from an outside of the housing so that, when the housing is in the target location, the target area is within tissue surrounding the lumen at a predetermined depth from a lumenal wall in combination with a temperature sensing element sensing data corresponding to a temperature of tissue in the target area and a processor controlling the heat generating element in response to the data sensed by the sensing element.

21 Claims, 9 Drawing Sheets

(56) References Cited

U.S. PATENT DOCUMENTS

| | | | |
|---|---|---|---|
| 7,470,241 B2* | 12/2008 | Weng et al. | 601/3 |
| 7,621,369 B2* | 11/2009 | Graber | 181/191 |
| 2002/0115922 A1* | 8/2002 | Waner et al. | 600/407 |
| 2004/0024347 A1 | 2/2004 | Wilson et al. | |
| 2004/0133109 A1* | 7/2004 | Crowley et al. | 600/438 |

* cited by examiner

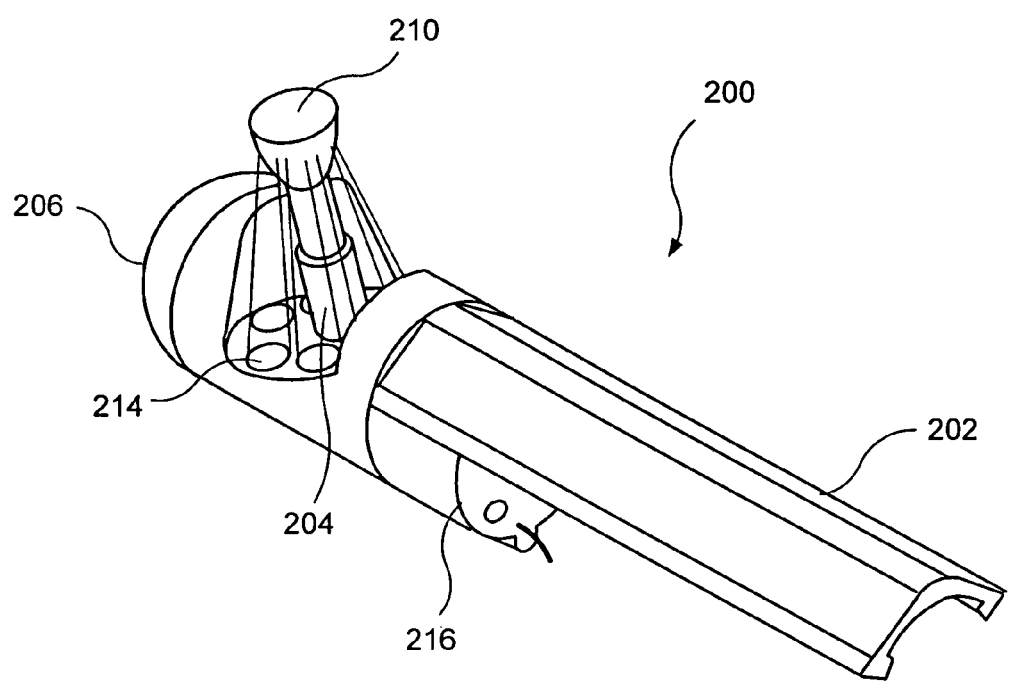
F I G. 3

DEVICE FOR THERMAL TREATMENT OF TISSUE AND FOR TEMPERATURE MEASUREMENT OF TISSUE PROVIDING FEEDBACK

BACKGROUND

Many medical procedures involve the application of heat to tissue to, for example, shrink or necrose or otherwise alter the properties of the tissue. Many of these procedures require one or more incisions to reach the target tissue increasing patient discomfort as well as the risk of complications.

Monitoring of these procedures has proven difficult. For example, if it is desirable to heat the target tissue to within a desired temperature range for a desired period of time, it may be necessary to provide sensors that monitor these parameters or which monitor data corresponding to these parameters. Also, in some cases, it may be necessary to monitor the target tissue to make certain that the heat applied to a target tissue does not exceed a maximum temperature. If possible, it is desirable to employ sensors (e.g., sensors for monitoring tissue temperature) which operate non-invasively.

In addition, available non-invasive heating methods show varying degrees of success. Methods employing radio frequency (RF), high intensity ultrasound, microwaves, optical and laser energy are available to heat tissue. However, in many cases a surgical procedure is necessary to bring the device supplying any of these types of energy into operative proximity to the target tissue. Furthermore, as it is possible to heat target tissue to a temperature outside an optimal or safe range using these methods, monitoring and adjusting the heating of the tissue enhances the results of the procedures.

SUMMARY OF THE INVENTION

The present invention is directed to a device for heating tissue, comprising a housing sized for insertion through a naturally occurring body orifice to a target location within a lumen and a heat generating element within the housing focusing thermal energy on a target area separated from an outside of the housing so that, when the housing is in the target location, the target area is within tissue surrounding the lumen at a predetermined depth from a lumenal wall in combination with a temperature sensing element sensing data corresponding to a temperature of tissue in the target area and a processor controlling the heat generating element in response to the data sensed by the sensing element.

BRIEF DESCRIPTION OF DRAWINGS

FIG. 3 shows a second embodiment of the heating device with monitoring sensors according to the present invention;

DETAILED DESCRIPTION

Figure 1:
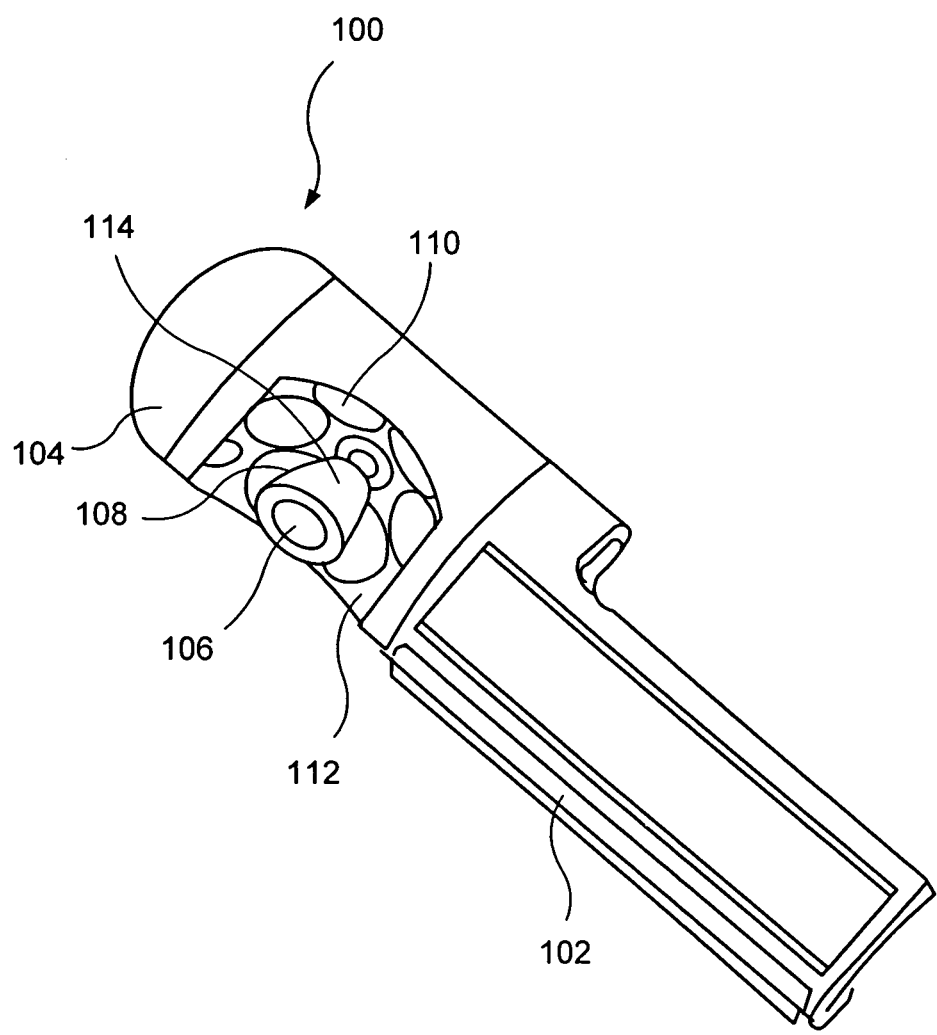
FIG. 1 shows a perspective view of an embodiment of a heating device with monitoring sensors according to the present invention.

The present invention may be further understood with reference to the following description and the appended drawings, wherein like elements are referred to with the same reference numerals. The invention relates to devices for heating tissue. More particularly, the present invention relates to a system for heating tissue and monitoring an amount of heating taking place to determine the heating power necessary to maintain a temperature of the target tissue within a predetermined range.

An exemplary procedure involves the heating of tissues near the bladder, such as the endopelvic fascia, to treat the symptoms of certain types of incontinence. Denaturing of the collagen in the target tissue through heating causes the tissue to shrink, tightening the tissue around the bladder and returning the bladder to a more natural position within the pelvis. By properly selecting the location and amount of shrinking, it is possible to significantly or even completely relieve the symptoms of incontinence with a minimally invasive approach. Other applications of thermal therapy include treatments for fecal incontinence, skin wrinkles and gastro esophageal reflux disease (GERD).

Another exemplary procedure involves the heating of excess prostate tissue. It is common for the prostate gland to become enlarged as a man ages. Severe enlargement may cause urine retention and strain on the bladder, which may lead to urinary tract infections, bladder or kidney damage, and incontinence. Thermal treatment of the excess prostate tissue provides a noninvasive alternative to surgery, as well as drug treatment, which is not always effective. The system heats and destroys target tissue via a naturally occurring orifice such as the rectum or urethra.

Other procedures, such as those requiring the formation of a lesion or for the removal of an abnormal growth (e.g., a tumor) involve heating of tissue to temperatures sufficient to cause necrosis. While carrying out the various procedures that utilize heating of target tissue, it is important to monitor the amount of heating taking place in the tissue. As described above, accurate feedback regarding the heating of the target tissue enhances the ability of the person performing the procedure to determine whether tissue is being subjected to temperatures outside a desired or safe range and whether a desired degree of tissue heating has been achieved.

The embodiments of the present invention provide a noninvasive thermal treatment for internal tissue of a patient. The system provides for either high intensity heating of target tissue (e.g., to generate a lesion) or lower intensity heating for other therapeutic purposes. The system is also designed to maintain a pre-determined temperature within the target tissue by remotely measuring the tissue's temperature and using the temperature data to adjust output power. In effect, a feedback mechanism is provided to control the amount of energy delivered to the target tissue based on the measured temperature of the tissue. Both the energy delivery and the temperature measurement are preferably carried out remotely, without penetrating the tissue.

Current temperature monitoring procedures utilize temperature sensing elements inserted within the target tissue. For example, interstitial RF electrodes manufactured by Rita Medical™ comprise thermocouples attached to the electrodes, that sense the temperature within the target tissue. However, this type of temperature sensor which is integral with the electrodes is useful only in more invasive procedures in which the electrodes are inserted into the tissue.

In one exemplary embodiment, an ultrasound transducer is used to listen to thermal noise generated within the heated tissue with an intensity of this noise increasing in intensity as the temperature increases. The data from this ultrasound transducer is processed electronically to obtain more information on the condition of target tissue below the surface including the temperature of the tissue.

The exemplary embodiments of the invention described herein refer principally to a tissue heating system employing temperature feedback obtained minimally invasively, for example, via an ultrasound transducer. In alternative embodiments, methods of remotely measuring the temperature of target tissue include, for example, optical imaging of the infrared spectrum and inserting a thermocouple through a portion of tissue to the target tissue.

The surgical heat treatment device according to embodiments of the present invention combines elements for remote energy delivery to the target tissue and elements for minimally invasively sensing the temperature of the target tissue. FIG. 1 shows a device 100 according to an exemplary embodiment of the invention including a high intensity ultrasound device for use, for example, in the treatment of female stress urinary incontinence (SUI). The device 100 is sized and shaped for placement in the vaginal canal to deliver energy to the endopelvic fascia located beyond the vaginal wall. This heating causes collagen in the tissue of the fascia to denature and shrink, tightening the tissue and restricting the mobility of the urethra and/or the bladder improving continence.

The exemplary embodiment shown in FIG. 1 also includes a temperature sensing element, such as an ultrasound transducer. The heating device 100 may be used more generally in a body lumen to heat tissue that would otherwise be reachable only surgically. Alternatively, devices similar to the heating device 100 maybe used externally to heat tissue below the surface of the skin without insertion of the device into a body lumen. According to the exemplary embodiment, the heating device 100 comprises a housing 102 which is preferably shaped and sized for insertion into a target body lumen (e.g., the vaginal canal) or any of a group of target body lumens. The device 100 also preferably includes a handle which, when the device 100 is inserted into a body lumen, remains outside the lumen accessible to the user. Heating energy is preferably generated near a distal end 104 of the device 100, in proximity to the target tissue. The distal end 104 according to this embodiment includes an acoustic reflector 114 designed to direct and shape an acoustic beam generated, for example, by high intensity transducers 110. The transducers 110 are preferably arranged in an array that cooperates with the acoustic reflector 114 to focus the acoustic energy at a desired point or along a desired line or curve separated from the transducers 110 by a predetermined distance. Those skilled in the art will understand that the predetermined distance is preferably substantially equal to a depth of the target tissue beneath of wall of the body lumen into which the device 100 is to be inserted plus a distance from the transducers 110 to a portion of an outer surface of the device 100 which, when the device 100 is in a desired position, is located between the transducers 110 and the target tissue. Furthermore, those skilled in the art will understand that the predetermined distance may vary in any desired manner along a line, curve or other path of heating, for example, to mirror changes in depth of target tissue along this heating path.

A sonolucent dome 112, transparent to acoustic energy, is preferably provided to cover the elements within the acoustic reflector 114 including the array of transducers 110. The dome 112 isolates the transducers 110 and any additional components therein from the surrounding environment and provides a cavity in which an acoustic coupling fluid may be held. For example, water or another acoustically appropriate liquid may flow between the dome 112 and the acoustic reflector 114 to increase the efficiency of energy transfer to the target tissue and the sensitivity of the temperature measuring system. That is, as would be understood by those skilled in the art, the liquid flowing within the dome 112 is selected to show acoustic transfer properties significantly superior to the properties of a medium which would otherwise fill the space within the dome 112 between the transducers 110 and the outer surface of the dome 112 to mitigate the attenuation of ultrasound signals within the dome 112.

A temperature sensing element 108 according to this embodiment includes a receiver ultrasound transducer 106 measuring the temperature of the tissue at a predetermined distance or distances from the surface of the device 100 which distance(s) preferably correspond to a depth of the target tissue heated by the transducers 110. The ultrasound transducer 106 receives noise generated by the heating of tissue and transmits this data to a data acquisition system and analyzes the data to determine an amount of thermal acoustic radiation from the target tissue. As described in the "Experimental Study of the Potential of Multichannel Acoustic Thermotomography" conducted by the Institute of Applied Physics of the Russian Academy of Sciences, internal temperatures of biological tissues can be measured based on the recording of acoustic radiation caused by the thermal motion of atoms and molecules of the medium. The intensity of the received signal is proportional to the acoustical brightness temperature (temperature and sound absorption) of the emitting object. Thus, it is possible to map the field of internal temperatures by measuring the intensity of radiation that arrives from different directions. An exemplary system to monitor temperature in this manner includes a computer programmed to analyze the signal generated by the ultrasound transducer 106 and to compute a tissue temperature from the signal.

Figure 2:
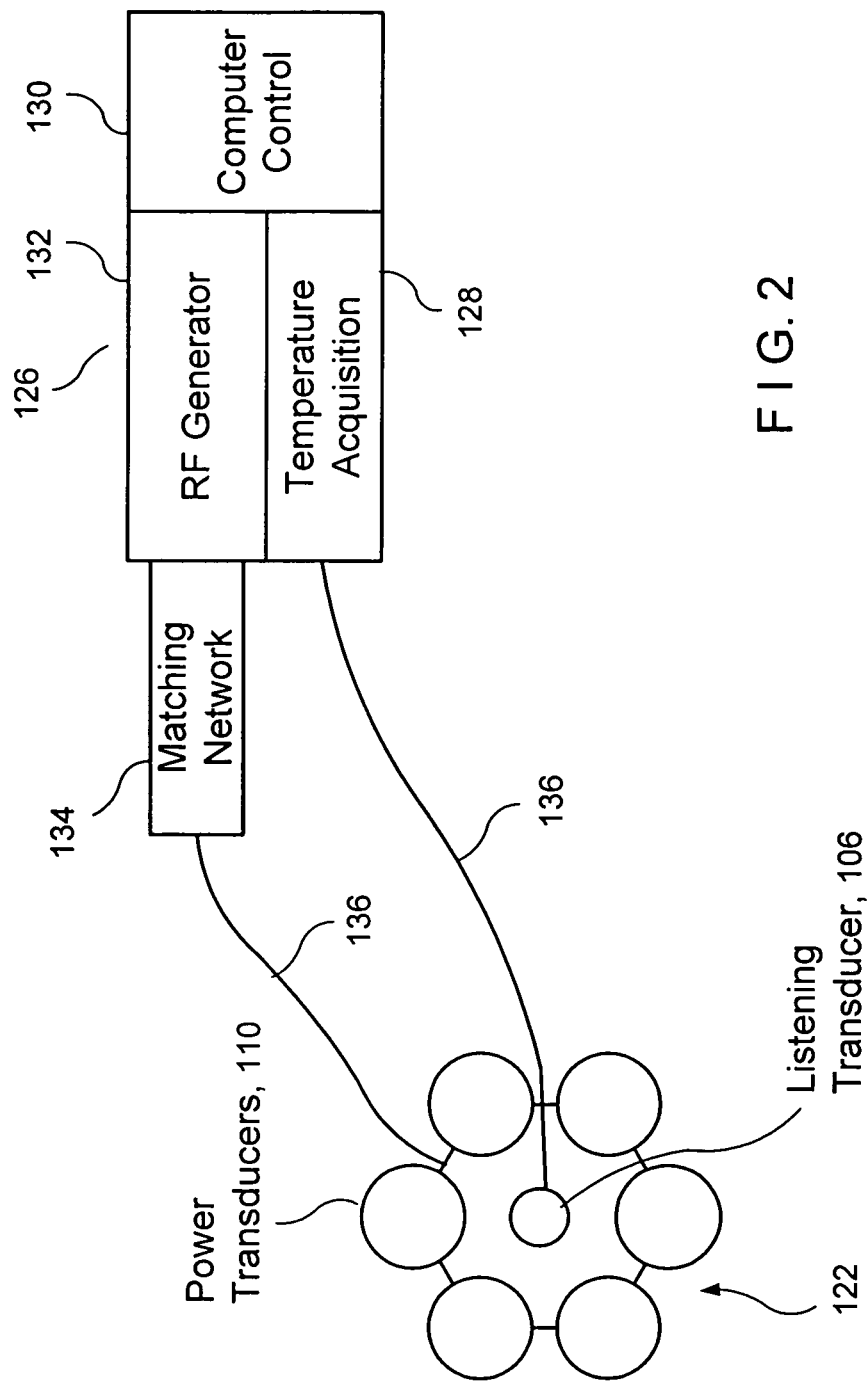
FIG. 2 shows a schematic diagram of the heating elements and monitoring sensors of the heating device shown in FIG. 1.

FIG. 2 shows a schematic representation of the control system for the heating device 100. The acoustic hardware 122 is connected to an electronic network 132 via electrical connectors 136. The electronic network 132 may be located in the distal end 104 of the device 100, under the acoustic reflector 114, or may be remote from the distal end 104. The power transducers 110 within the device 100 are connected to a matching network 134 and then to an RF generator 132 producing electric power in the form of a radio frequency of between about 1 MHz and about 10 MHz. The receiver ultrasound transducer 106 is connected to a temperature acquisition module 128 processing sensed signals and computing a resulting temperature within the target tissue.

The temperature acquisition module 128 and the RF generator 126 are both connected to a computer control 130 that manages operation of the heating device 100. For example, when the temperature acquisition module 128 senses that the temperature within the target tissue is above a target temperature or outside a desired range, the computer control 130 commands the RF generator 132 to suspend or to reduce the power emitted by the power transducers 110. Conversely, if the temperature sensed in the target tissue is below an optimal range or target temperature for a current procedure, the computer control 130 commands an increase in the power provided by the RF generator 132. Optionally, whether the temperature is above or below an optimum temperature or temperature range, the computer control 130 may generate an alarm or other signal to the user indicating the condition and/or suggesting appropriate action (e.g., increasing, decreasing or suspending the heating of tissue).

In a different embodiment according to the invention, the receiver transducer 106 is connected to an ultrasound system operating, for example, in a pulse-echo response mode. In this mode the transducer 106 would act as a transmitter-receiver. It would take the electronic pulses, generated by the system, convert them into mechanical vibration and send it into tissues. Then it would receive the echo from the tissues, convert it into electronic signal and sending it back to the system. The system would analyze these signals and determine the temperature of the tissues by, for example detecting and calculating the speed of propagation of mechanical waves through the tissue. It is known that this speed changes as a function of temperature. The computer control 130 is preferably programmed to execute an algorithm processing the signals to extract temperature data from the imaging signal.

In yet another embodiment, the temperature sensing element 108 comprises an optical device instead of the receiver transducer 106. This optical device may comprise, for example, an infrared sensor measuring an intensity of an infrared radiation, produced by the heated tissue, which would correspond to the temperature of tissue while the computer control 130 and the temperature acquisition module 128 executed programming to calculate temperature at a predetermined depth within the tissue based on the data sensed by the optical device.

Alternatively, in certain procedures where tissue is heated remotely (by delivering energy from a probe which does not penetrate the tissue), it may be desirable to insert a sensor into the tissue to sense the temperature of the target tissue. For example, if the target tissue is to be heated to the point of necrosis, the additional expense and complexity of remote temperature sensing may not be necessary. As indicated above, feedback corresponding to the temperature of the target tissue may be used to maintain the temperature of the target tissue within a target or optimal range, for example, under computer control. The direct measurement of target tissue temperature through the inserted sensor allows the computer to monitor and control the heating of the target tissue without the more complex temperature acquisition system described above.

Figure 4:
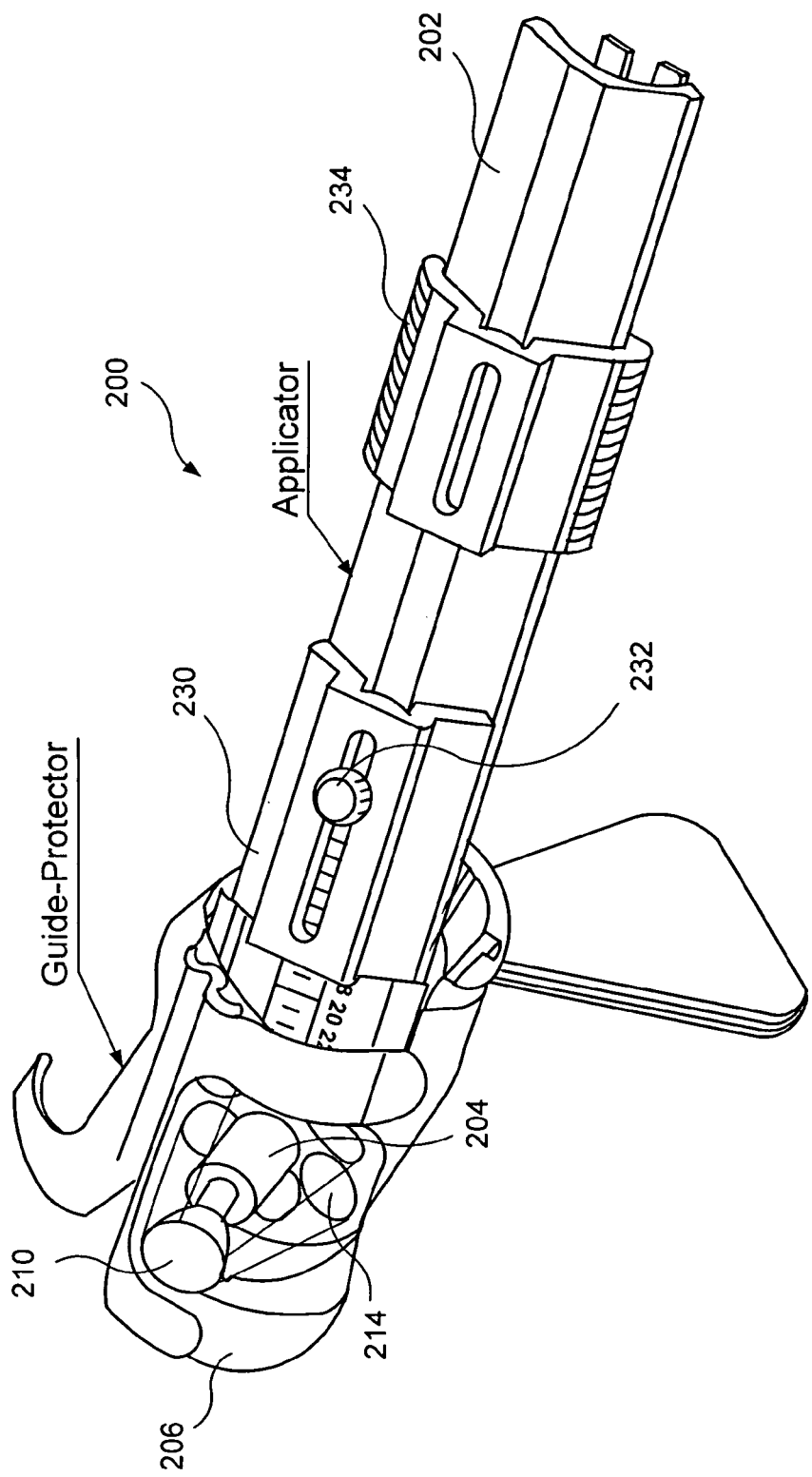
FIG. 4 shows a perspective view of the second embodiment of the heating device with monitoring sensors according to the present invention.
Figure 5:
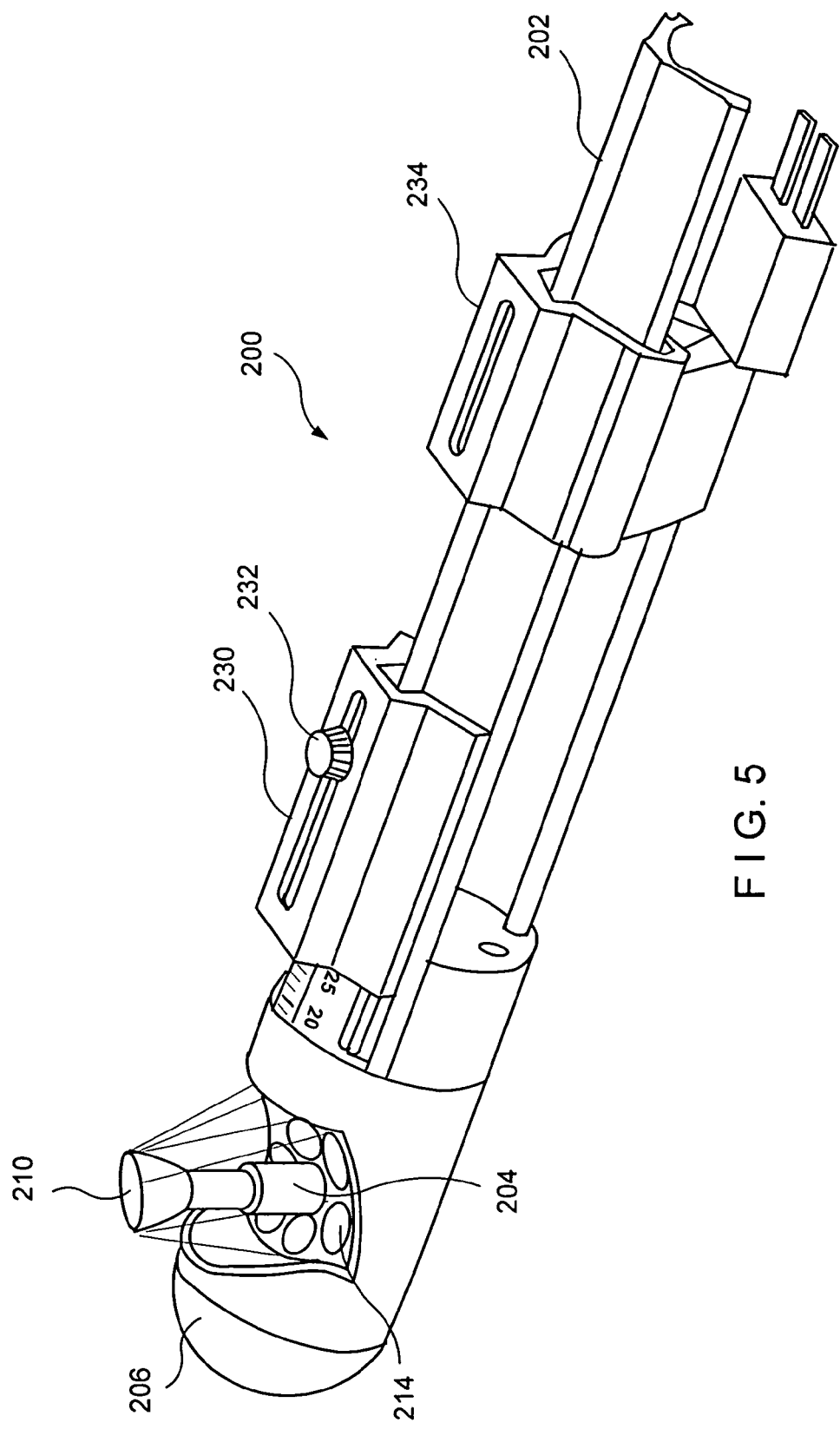
FIG. 5 shows a perspective view of the second embodiment of the heating device with positioning and temperature measuring systems.
Figure 6:
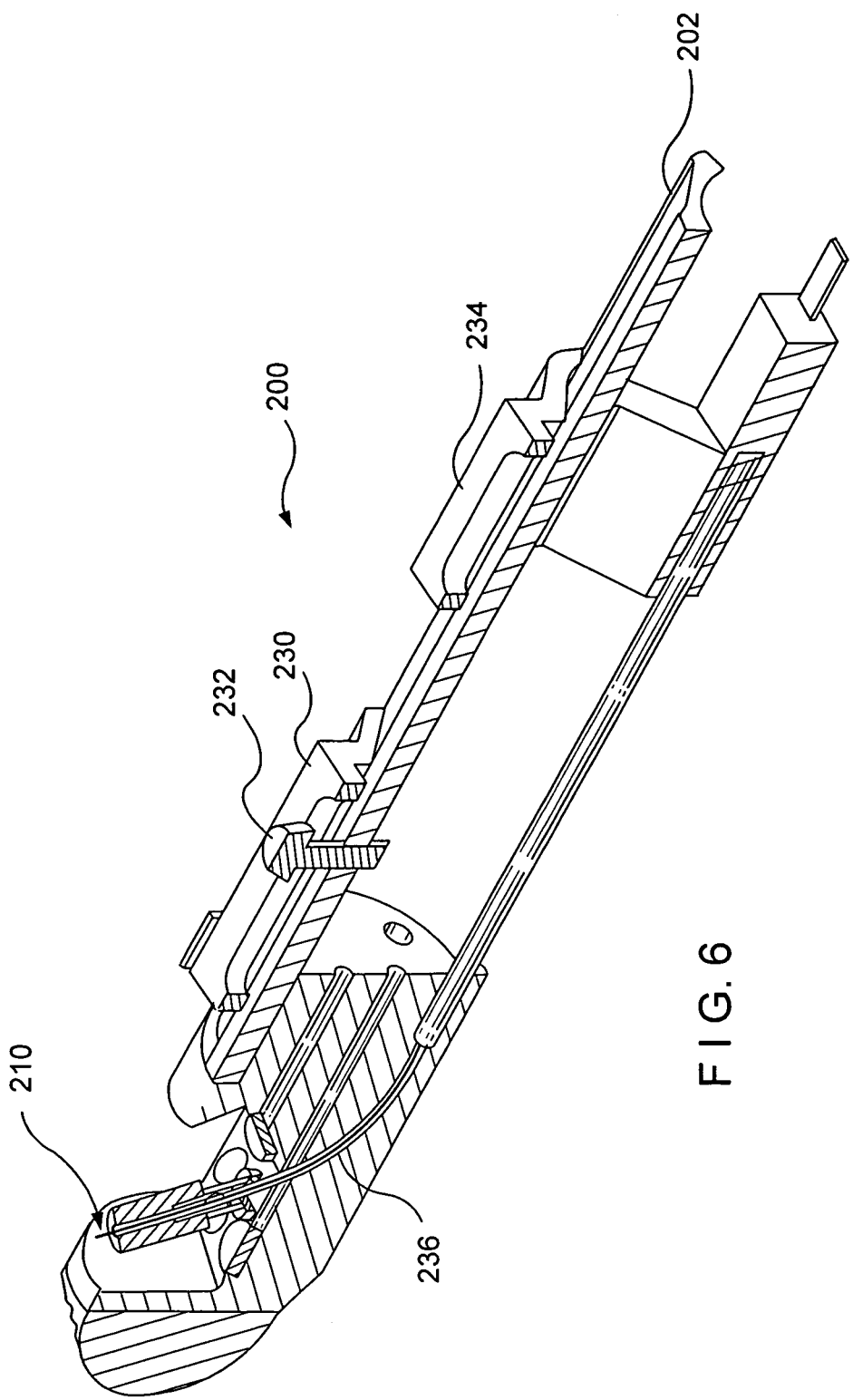
FIG. 6 shows a cross-sectional perspective view of the heating device with positioning and temperature measuring systems.

FIGS. 3-9 show an exemplary device 200 including a thermocouple probe 210 which, when the device 200 is in a desired position within a body lumen, may be deployed to penetrate the target tissue. Similarly to the device 100, the device 200 is sized and shaped for insertion into a target body lumen, such as the vaginal canal, to heat target tissue adjacent to a wall of the target body lumen. In one exemplary embodiment, the device 200 is used to heat the endopelvic fascia located just below the surface of the vaginal mucosa, to treat SUI (FIG. 4). As shown in FIG. 5, the device 200 may also include a sliding stop 230, a locking screw 232 and a thermocouple slide 234 for proper positioning and temperature measuring. In this exemplary embodiment, the heating is generated by an array of ultrasound crystals 214 located in an acoustic reflector 204 adapted to focus the acoustic energy at a point (or along a line, curve or other heating path) beneath a surface of the lumen wall.

As indicated above, acoustic energy delivered by the crystal array 214 is controlled in response to the temperature measured within the target tissue. According to this exemplary embodiment, the temperature measurement is made by a small diameter thermocouple probe 210 coupled to any known deployment mechanism which, when activated, advances the probe 210 from within a tip 206 of the device 200 to extend out of the device 200 to a point within the tissue in or adjacent to an area on which the heating energy of the device 200 is focused. In the exemplary SUI procedure according to this embodiment, the thermocouple probe 210 is advanced by the deployment mechanism through the wall of the vaginal canal to the depth of the target portion of the endopelvic fascia to directly measure the heating achieved by the device 200.

More specifically, the deployment mechanism includes a tube 202 extending from a handle of the device 200, where it forms a gradual bend from a longitudinal axis of the handle, through the center of the crystal array 214. Those skilled in the art will understand that the tube 202 may be formed of any suitable material such as, for example, stainless steel, nitinol or a polymer such as polyimide. A small diameter thermocouple 210 extends through the tube 202 with a distal tip of the thermocouple 210 extending out of a distal opening of the tube 202. In one exemplary embodiment, the thermocouple 210 has a diameter of about 0.020 inches, so that it causes only a small puncture when advanced into the tissue. As would be understood by those skilled in the art, standard thermocouple diameters range from about 0.010" to about 0.25". The bend in the tube 202 is selected so that, when the probe 210 is advanced distally therethrough, a distal end of the probe 210 is aimed at the tissue of the lumen wall along a path intersecting with an area where the temperature is to be monitored (does not have to be in focus) of focus of the energy from the crystal array 214. Those skilled in the art will understand that, when the device 200 is in the desired location within the lumen, this area of focus will be within the target tissue.

Figure 7:
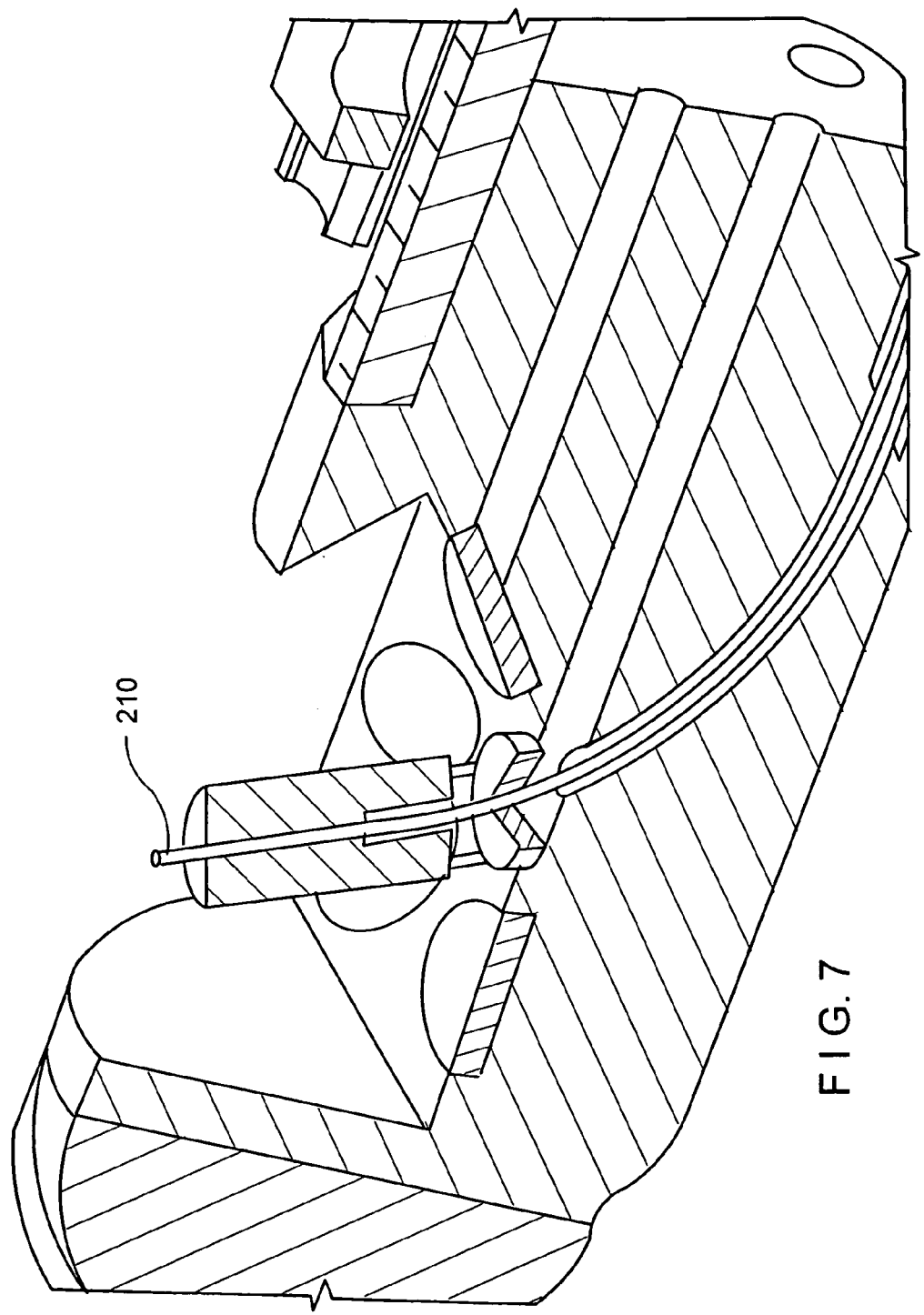
FIG. 7 shows a cross-section of the distal portion of the heating device.
Figure 8:
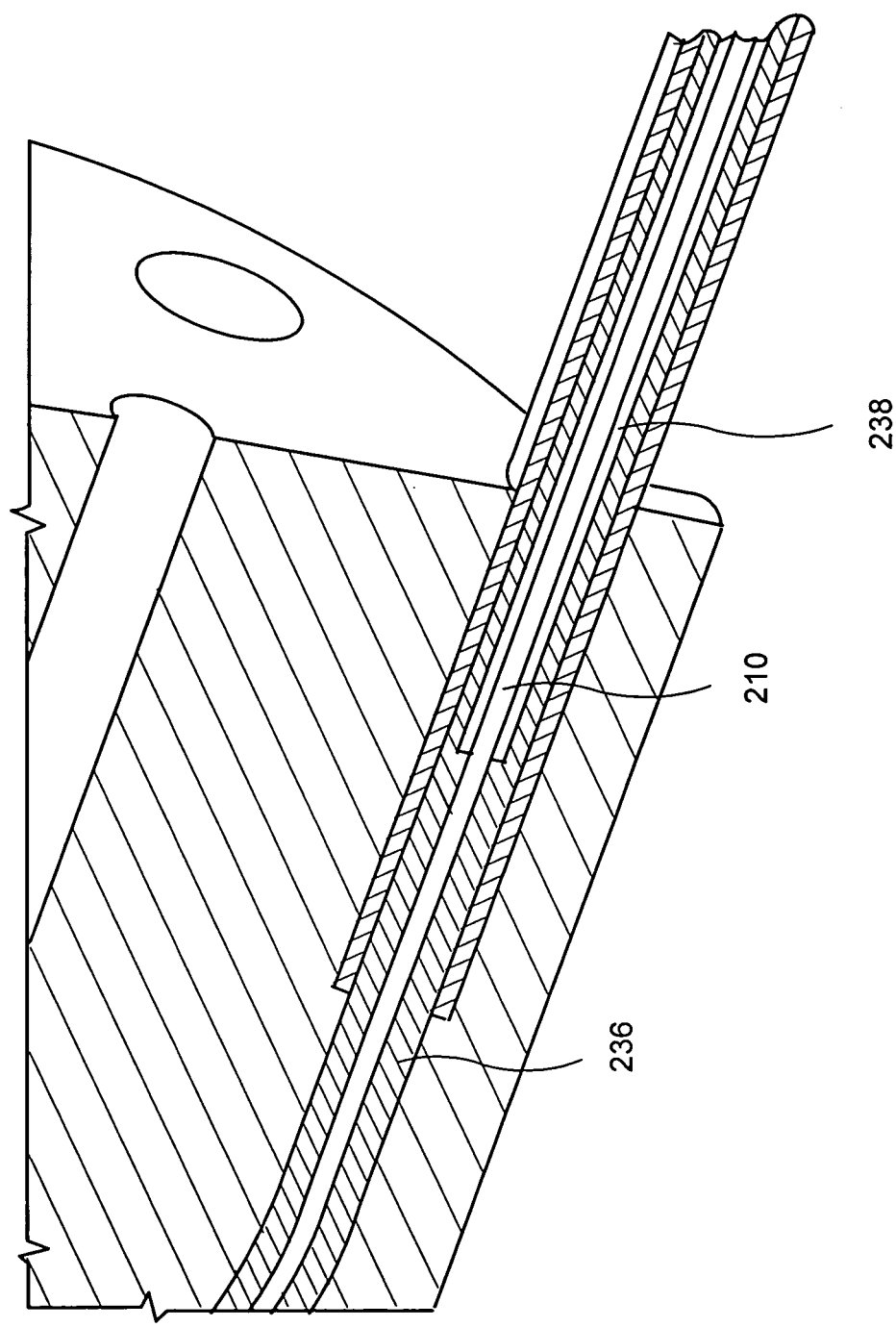
FIG. 8 shows a cross-section of the middle portion of the heating device.
Figure 9:
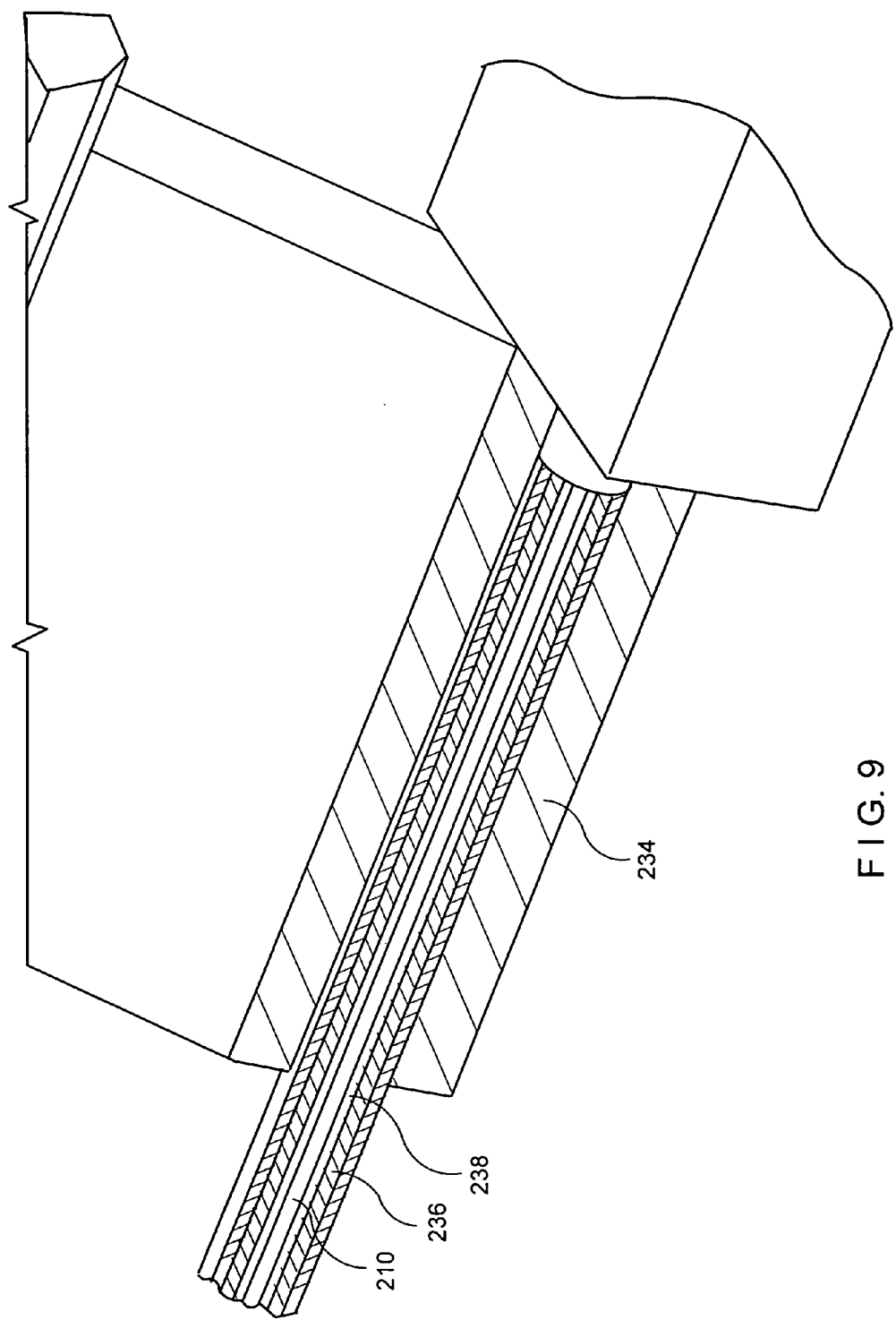
FIG. 9 shows a cross-section of the proximal portion of the heating device.

Once the device 200 has been positioned at a desired location in a lumen, the tube 202 is advanced to push the distal end of the thermocouple probe 210 into the tissue to the area of focus of the energy from the crystal array 214. The actuation to place the thermocouple probe 210 in the target tissue may take place by holding the tube 202 stationary and advancing the thermocouple 210 through the tube, so that it extends into the tissue. As shown in FIGS. 7-9, the thermocouple 210 is advanced through the tube 202 by pushing the thermocouple slide 234 forward. A guiding tubing 236 is locked with the device 200 and the thermocouple 210 is reinforced by a supporting tubing 238, which slides inside of the guiding tubing 236. FIG. 9 shows proximal portion of the device 200 with the thermocouple slide 234 in the forward position. The thermocouple 210 is locked with the thermocouple slide 234, with clearance between the inner surface of the slide 234 and the outer diameter of the guiding tubing 236. Alternatively, the thermocouple probe 210 may be fixed to the tube 202, and both components may be advanced together through the device 200 toward the tissue until the tip of the thermocouple probe 210 penetrates the target tissue to a desired depth. This depth of penetration may be measured by, for example, markings on the thermocouple probe 210, the tube 202 or both.

The exemplary embodiments of the present invention described above are directed principally to an acoustic heating probe for treating stress urinary incontinence. However, other embodiments of the invention may be devised that use alternative sources of energy to heat target tissue to treat SUI or other conditions. For example, an alternative temperature feedback system for thermal therapy may use a microwave generator, laser light or a radio-frequency generator as the power source to heat tissue. In addition, the temperature measurement may be carried out with a device other than a thermocouple or receiver ultrasound transducer as described above. For example, a low mass, non-absorbing and non-self heating fluoroptic device may be used to measure target tissue temperature. These devices, manufactured by Fluxtron Corporation, have an optical fluorescent sensor on the end of a fiberoptic cable. The specter of fluorescence depends on the temperature. The temperature is determined by analyzing the specter of the fluorescence. This type of temperature sensor is especially well suited for devices that deliver radio-frequency or laser energy to target tissue.

The present invention has been described with reference to specific exemplary embodiments. Those skilled in the art will understand that changes may be made in details, particularly in matters of shape, size, material and arrangement of parts. For example, the power supplies, processors and any output devices need not be housed within the probe itself. Any or all of these elements may be part of separate elements. Accordingly, various modifications and changes may be made to the embodiments described herein. The specifications and drawings are, therefore, to be regarded in an illustrative rather than a restrictive sense.

What is claimed is:

1. A device for heating tissue, comprising:
a housing sized for insertion through a naturally occurring body orifice to a target location within a lumen;
a heat generating element focusing thermal energy on a target area separated from an outside of the housing so that, when the housing is in the target location, the target area is within tissue surrounding the lumen at a predetermined depth from a lumenal wall wherein the heat generating element comprises an array of ultrasound transducers positioned within the housing and an acoustic reflector positioned over an outer surface of the housing and over the array of transducers, the acoustic reflector extending away from the housing in a first direction by a first predetermined distance toward the target area so that acoustic energy from the ultrasound transducers is focused away from the transducers in the first direction by a second predetermined distance greater than the first predetermined distance;
a temperature sensing element sensing data corresponding to a temperature of tissue in the target area; and
a processor controlling the heat generating element in response to the data sensed by the sensing element.

2. The device according to claim 1, wherein the temperature sensing element comprises an ultrasound listening transducer.

3. The device according to claim 1, wherein the processor includes a temperature acquisition module computing target tissue temperature based on the data sensed by the temperature sensing element.

4. The device according to claim 1, further comprising an RF generator controlled by the processor to power the heat generating element.

5. The device according to claim 1, wherein the housing comprises a sonolucent dome enclosing the array of ultrasound transducers.

6. The device according to claim 5, further comprising an acoustic coupler fluid within the sonolucent dome.

7. The device according to claim 1, wherein the temperature sensing element comprises a thermocouple adapted for deployment from the housing into the target area.

8. The device according to claim 7, wherein a diameter of the thermocouple is no more than approximately 0.02 inches.

9. The device according to claim 7, further comprising a tube through which the thermocouple extends, the tube being shaped so that, upon deployment of the thermocouple, a distal end of the thermocouple is directed to the target area.

10. The device according to claim 1, wherein the heat generating element comprises at least one of a microwave generator, a laser generator and a radio-frequency generator.

11. The device according to claim 1, wherein the temperature sensing element comprises at least one of an imaging ultrasound transducer, an infrared optical imaging element, and a fluoroptic probe.

12. A device for treating urinary incontinence, comprising:
a probe insertable into a vaginal canal, the probe comprising an energy delivery element including an acoustic reflector positioned over an outer wall of the probe and extending away from the probe in a first direction by a first predetermined distance toward a target portion of an endopelvic fascia of the patient so that acoustic energy from the energy delivery element is focused away from the probe in the first direction by a second predetermined distance greater than the first predetermined distance and a temperature measuring element generating a signal corresponding to a temperature of the target portion of the endopelvic fascia; and
a processor varying an intensity of energy delivered by the energy delivery element to maintain a temperature of the target portion of the endopelvic fascia within a predetermined range.

13. The device according to claim 12, further comprising a temperature acquisition module of the electronic processor adapted to compute the temperature of the endopelvic fascia from the signal of the temperature measuring element.

14. The device according to claim 12, wherein the energy delivery element comprises an array of high intensity ultrasound transducers.

15. The device according to claim 14, further comprising a sonolucent dome enclosing the ultrasound transducers and an acoustic coupling fluid therein.

16. The device according to claim 12, wherein the temperature measuring element comprises an acoustic listening transducer.

17. The device according to claim 12, wherein the temperature measuring element comprises a thermocouple and a deploying mechanism for advancing the thermocouple into the target portion of the endopelvic fascia.

18. The device according to claim 17, wherein a diameter of the thermocouple is no greater than approximately 0.02 inches.

19. The device according to claim 17, wherein the deploying mechanism includes a tube extending within which the thermocouple is received, the tube being shaped so that, when the probe is in the desired location, one of advancing the tube distally relative to the probe and advancing the thermocouple distally relative to the tube guides the thermocouple to the target portion of the endopelvic fascia.

20. The device according to claim 19, wherein the tube is formed of one of stainless steel, nitinol and polyimide.

21. The device according to claim 1, wherein the array of transducers are arranged to form a cavity along an outer surface of the housing, the cavity being configured to house an acoustic coupling fluid therein.

\* \* \* \* \*